(12) United States Patent
Williams

(10) Patent No.: US 10,758,244 B2
(45) Date of Patent: *Sep. 1, 2020

(54) ENDOSCOPIC SURGICAL CLIP APPLIER

(71) Applicant: Covidien LP, Mansfield, MA (US)

(72) Inventor: Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 319 days.

This patent is subject to a terminal disclaimer.

(21) Appl. No.: 15/865,843

(22) Filed: Jan. 9, 2018

(65) Prior Publication Data
US 2018/0221028 A1    Aug. 9, 2018

Related U.S. Application Data

(60) Provisional application No. 62/455,090, filed on Feb. 6, 2017.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/282* (2013.01);
(Continued)

(58) Field of Classification Search
CPC ... A61B 1/3131; A61B 1/3132; A61B 17/122; A61B 17/1285; A61B 17/282;
(Continued)

(56) References Cited

U.S. PATENT DOCUMENTS 3,120,230 A    2/1964  Skold
3,363,628 A    1/1968  Wood
(Continued)

FOREIGN PATENT DOCUMENTS

AU    2013254887 A1   11/2013
CA       1163889 A    3/1984
(Continued)

OTHER PUBLICATIONS

European Office Action corresponding to European Appln. No. EP 16 15 9324.9 dated Aug. 7, 2017.
(Continued)

*Primary Examiner* — Jocelin C Tanner

(57) ABSTRACT

An endoscopic surgical clip applier includes an endoscopic assembly and a handle assembly. The endoscopic assembly includes a shaft assembly and a pair of jaw members. The handle assembly includes a housing, a fixed handle, a trigger, a drive bar, and a ratchet assembly. The ratchet assembly includes a first rack operatively coupled to the drive bar, the first rack defining a plurality of first rack teeth, wherein the first rack includes a first length between a distal end and a proximal end thereof, and a second rack operatively coupled to the drive bar, spaced apart from the first rack, the second rack defining a plurality of second rack teeth, wherein the second rack includes a second length between a distal end and a proximal end thereof, the second length of the second rack being less than the first length of the first rack.

17 Claims, 10 Drawing Sheets

(51) Int. Cl.
   *A61B 17/28*   (2006.01)
   *A61B 17/29*   (2006.01)
   *A61B 17/00*   (2006.01)
   *A61B 90/00*   (2016.01)
   *A61B 1/313*   (2006.01)

(52) U.S. Cl.
   CPC ... *A61B 1/3132* (2013.01); *A61B 2017/00407* (2013.01); *A61B 2017/294* (2013.01); *A61B 2017/2929* (2013.01); *A61B 2090/0807* (2016.02)

(58) Field of Classification Search
   CPC ...... A61B 2017/2929; A61B 2017/294; A61B 2017/12004; A61B 2090/0807
   See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |

(56) References Cited

U.S. PATENT DOCUMENTS

| | | |
|---|---|---|
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |

(56) References Cited

U.S. PATENT DOCUMENTS

| | | |
|---|---|---|
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |

(56) References Cited

U.S. PATENT DOCUMENTS

| | | |
|---|---|---|
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,887,553 B2 | 2/2011 | Lehman et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |

(56) References Cited

U.S. PATENT DOCUMENTS

| | | |
|---|---|---|
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,820 B2 | 9/2016 | Whiting |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,517,064 B2 | 12/2016 | Sarradon |
| 9,526,501 B2 | 12/2016 | Malkowski |
| 9,545,254 B2 | 1/2017 | Sorrentino et al. |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1* | 11/2004 | Shelton, IV ...... A61B 17/07207 227/175.1 |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |

(56) References Cited

U.S. PATENT DOCUMENTS

| | | |
|---|---|---|
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0194903 A1 | 7/2014 | Malkowski et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0045816 A1 | 2/2015 | Aranyi et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1* | 8/2018 | Baril .................. A61B 17/105 |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0 406 724 A1 | 1/1991 |
| EP | 0514139 A2 | 11/1992 |
| EP | 0514139 A3 | 3/1993 |
| EP | 0 732 078 A2 | 9/1996 |
| EP | 1769757 A1 | 4/2007 |
| GB | 2073022 A | 10/1981 |
| JP | 2003-033361 A | 2/2003 |
| JP | 2006-154230 A | 6/2006 |
| JP | 2006-277221 A | 10/2006 |
| JP | 2008-017876 A | 1/2008 |
| WO | 0042922 A1 | 7/2000 |
| WO | 2001-66001 A2 | 9/2001 |
| WO | 2001-67965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Chinese First Office Action corresponding to Chinese Appln. No. CN 2014104295806 dated Aug. 31, 2017.

Extended European Search Report corresponding to European Appln. No. EP 17 17 3508.7 dated Sep. 29, 2017.

Chinese Second Office Action corresponding to Chinese Appln. No. CN 201410076318.8 dated Oct. 10, 2017.

Extended European Search Report corresponding to European Appln. No. EP 17 18 0570.8 dated Dec. 6, 2017.

Extended European Search Report corresponding to counterpart Patent Appln. EP 18 15 5158.1 dated Jun. 28, 2018.

The extended European Search Report corresponding to European Application No. EP 07 25 3905.9, completed Jan. 29, 2008; dated Feb. 7, 2008; (7 Pages).

International Search Report corresponding to International Application No. PCT-US08-58185, completed Sep. 4, 2008; dated Sep. 9, 2008; (2 Pages).

The International Search Report corresponding to International Application No. PCT-US08-59859, completed Sep. 14, 2008; dated Sep. 18, 2008; (2 Pages).

The extended European Search Report corresponding to European Application No. EP 07 25 3807.7, completed Nov. 7, 2008; dated Nov. 26, 2008; (11 Pages).

The extended European Search Report corresponding to European Application No. EP 09 25 2049.3, completed Dec. 11, 2009; dated Jan. 12, 2010; (3 Pages).

The extended European Search Report corresponding to European Application No. EP 09 25 2050.1, completed Dec. 23, 2009; dated Jan. 21, 2010; (3 Pages).

The extended European Search Report corresponding to European Application No. EP 09 25 2051.9, completed Dec. 21, 2009; dated Jan. 28, 2010; (3 Pages).

The extended European Search Report corresponding to European Application No. EP 09 25 2052.7, completed Nov. 16, 2009; dated Nov. 24, 2009; (3 Pages).

The extended European Search Report corresponding to European Application No. EP 09 25 2053.5, completed Nov. 24, 2009; dated Dec. 1, 2009; (3 Pages).

(56) References Cited

OTHER PUBLICATIONS

The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
European Office Action corresponding to EP 12 152 989.5 dated May 4, 2015.

(56) References Cited

OTHER PUBLICATIONS

Australian Office Action corresponding to AU 2009212759 dated May 7, 2015.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.

* cited by examiner

ENDOSCOPIC SURGICAL CLIP APPLIER

CROSS-REFERENCE TO RELATED APPLICATION

This application claims the benefit of and priority to U.S. Provisional Patent Application No. 62/455,090 filed Feb. 6, 2017, the entire disclosure of which is incorporated by reference herein.

BACKGROUND

Technical Field

The present disclosure relates generally to surgical clip appliers. More particularly, the present disclosure relates to endoscopic surgical clip appliers having a release switch for a ratchet assembly thereof.

Description of Related Art

Endoscopic surgical staplers and surgical clip appliers are used for a number of minimally invasive or endoscopic surgical procedures. Typically in a minimally invasive surgical procedure, a tube or cannula device is extended into the patient's body through the entrance incision to provide an access port. The port allows the surgeon to insert a number of different surgical instruments therethrough for performing surgical procedures far removed from the incision.

Endoscopic surgical clip appliers are capable of applying a single or multiple surgical clips during a minimally invasive surgical procedure. Applying surgical clips usually involves compressing the clip over a vessel. Once applied to the vessel, the compressed surgical clip terminates the flow of fluid therethrough. Terminating the flow of fluid through a vessel typically requires complete formation of the surgical clip.

During certain endoscopic procedures, it may be desirable and/or necessary to partially form clips. For example, a partially formed clip may be used to secure a catheter around tissue during a cholangiogram or other medical procedure.

Accordingly, a need exists for endoscopic surgical clip appliers that provide a clinician with a convenient way to partially form surgical clips.

SUMMARY

The present disclosure relates to endoscopic surgical clip appliers that allow a clinician to choose whether to partially or completely form surgical clips.

According to an aspect of the present disclosure, an endoscopic surgical clip applier includes an endoscopic assembly and a handle assembly. The endoscopic assembly includes a shaft assembly and a pair of jaw members operatively coupled to, and extending from the shaft assembly. The handle assembly includes a housing selectively connectable to the endoscopic assembly. A fixed handle extends from the housing, and a trigger is pivotally connected to the fixed handle. A drive bar is disposed within the housing of the handle assembly and is operatively coupled to the trigger and to the pair of jaw members to move the pair of jaw members between a spaced apart configuration and an approximated configuration upon actuation of the trigger. A ratchet assembly is also disposed within the housing of the handle assembly. The ratchet assembly includes a first rack operatively coupled to the drive bar. The first rack defines a plurality of first rack teeth, has a distal end and a proximal end, and includes a first length between the distal end and the proximal end thereof. A second rack is operatively coupled to the drive bar, spaced apart from the first rack. The second rack defines a plurality of second rack teeth, has a distal end and a proximal end, and includes a second length between the distal end and the proximal end thereof. The second length of the second rack is less than the first length of the first rack.

In embodiments, the ratchet assembly further includes a first pawl mounted within the housing of the handle assembly, the first pawl being selectively engagable with the plurality of first rack teeth of the first rack in a first position thereof.

In embodiments, the ratchet assembly further includes a second pawl mounted within the housing of the handle assembly, the second pawl being selectively engageable with the plurality of second rack teeth of the second rack in a first position thereof.

In embodiments, the ratchet assembly further includes a distal well disposed adjacent the distal end of the first rack, wherein the first pawl is located in the distal well in an un-actuated position of the trigger.

In some embodiments, the ratchet assembly further includes a proximal well disposed between the proximal end of the first rack and the distal end of the second rack, wherein the second pawl is located in the proximal well in the un-actuated position of the trigger.

In embodiments, the first rack is disposed in a position distal of the second rack.

In embodiments, the ratchet assembly further includes a release switch at least partially supported within the housing of the handle assembly and operatively associated with the first pawl. The release switch is selectively actuatable to move the first pawl from the first position, wherein the first pawl is in registration with the plurality of first rack teeth of the first rack, to a second position, wherein the first pawl is out of registration with the plurality of first rack teeth of the first rack.

In embodiments, when the release switch is actuated, the second pawl maintains registration with the plurality of second rack teeth of the second rack, in the first position thereof, until the second pawl is disposed in the proximal well or until the second pawl is disposed proximally beyond the proximal end of the second rack.

In some embodiments, the drive bar is longitudinally movable upon actuation of the trigger, wherein as the drive bar is moved longitudinally in a first direction, and the release switch is not actuated, the first pawl and the second pawl are moved over the plurality of first rack teeth and the plurality of second rack teeth of the first and the second racks, respectively, such that longitudinal movement of the drive bar in a second, opposite, direction is prevented until the first pawl is disposed in the distal well and the second pawl is disposed in the proximal well or until the first pawl is disposed at the proximal end of the first rack and the second pawl is disposed proximally beyond the proximal end of the second rack.

In embodiments, the drive bar is longitudinally movable upon actuation of the trigger, wherein as the drive bar is moved longitudinally in a first direction, and the release switch is actuated to move the first pawl out of registration with the plurality of first rack teeth of the first rack, longitudinal movement of the drive bar in a second, opposite, direction is prevented until the second pawl is disposed in the proximal well or until the second pawl is disposed proximally beyond the proximal end of the second rack.

In embodiments, as the drive bar is moved longitudinally in the first direction, and the release switch is actuated to move the first pawl out of registration with the plurality of first rack teeth of the first rack, the second pawl is disposed beyond the proximal end of the second rack as the trigger reaches a partially actuated position, wherein the drive bar is longitudinally movable in the second, opposite, direction, as the trigger reaches a fully un-actuated position from the partially actuated position.

In embodiments, the endoscopic assembly further includes a plurality of surgical clips slidably disposed within the shaft assembly and selectively formable between the pair of jaw members, wherein when the first pawl is in the first position, the first pawl is in registration with the first rack disposed on the drive bar such that upon actuation of the trigger, the trigger is prevented from reversing the direction of movement thereof until the trigger is moved to a fully actuated position and a distal most surgical clip of the plurality of surgical clips is fully formed between the pair of jaw members.

In some embodiments, when the first pawl housing is in the second position, the first pawl is out of registration with the first rack disposed on the drive bar such that when the second pawl is disposed beyond the proximal end of the second rack and the trigger is moved to the partially actuated position, the trigger is capable of reversing the direction of movement thereof such that the distal most surgical clip of the plurality of surgical clips is partially formed between the pair of jaw members.

In embodiments, the ratchet assembly further includes a first pawl spring and a second pawl spring supported within the housing of the handle assembly. The first pawl spring is configured to bias the first pawl into engagement with the plurality of first rack teeth of the first rack, and the second pawl spring being is to bias the second pawl into engagement with the plurality of second rack teeth of the second rack.

In embodiments, the first pawl includes a lockout member extending therefrom. The lockout member selectively engages the release switch as the trigger moves to the fully un-actuated position, to prevent the release switch from moving the first pawl out of registration with the plurality of first rack teeth of the first rack, to the second position thereof.

In embodiments, the ratchet assembly further includes a release spring supported in the handle assembly. The release spring is operatively associated with the release switch and is biased to return the release switch to a home position such that the release switch is disengaged from the first pawl.

According to another aspect of the present disclosure, an endoscopic surgical clip applier includes an endoscopic assembly and a handle assembly. The endoscopic assembly includes a shaft assembly and a pair of jaw members operatively coupled to, and extending from the shaft assembly. The handle assembly includes a housing selectively connectable to the endoscopic assembly, a fixed handle extending from the housing, and a trigger pivotally connected to the fixed handle. A drive bar is disposed within the housing of the handle assembly and is operatively coupled to the trigger and the pair of jaw members to move the pair of jaw members between a spaced apart configuration and an approximated configuration upon actuation of the trigger. A ratchet assembly is also disposed within the housing of the handle assembly. The ratchet assembly includes a first rack defined on a top portion of the drive bar. The first rack includes a plurality of first rack teeth and has a distal end and a proximal end. A second rack is defined on the top portion of the drive bar. The second rack includes a plurality of second rack teeth and has a distal end and a proximal end. A first pawl is movably mounted within the handle assembly and is selectively engageable with the plurality of first rack teeth of the first rack. A second pawl is movably mounted within the handle assembly and is selectively engageable with the plurality of second rack teeth of the second rack. Upon movement of the trigger, a reversal of a direction of movement of the trigger is prohibited until the second pawl is disposed distally beyond the distal end of the second rack or proximally beyond the proximal end of the second rack.

BRIEF DESCRIPTION OF THE DRAWINGS

Particular embodiments of endoscopic surgical clip appliers are described herein with reference to the drawings wherein.

DETAILED DESCRIPTION OF EMBODIMENTS

Figure 1:
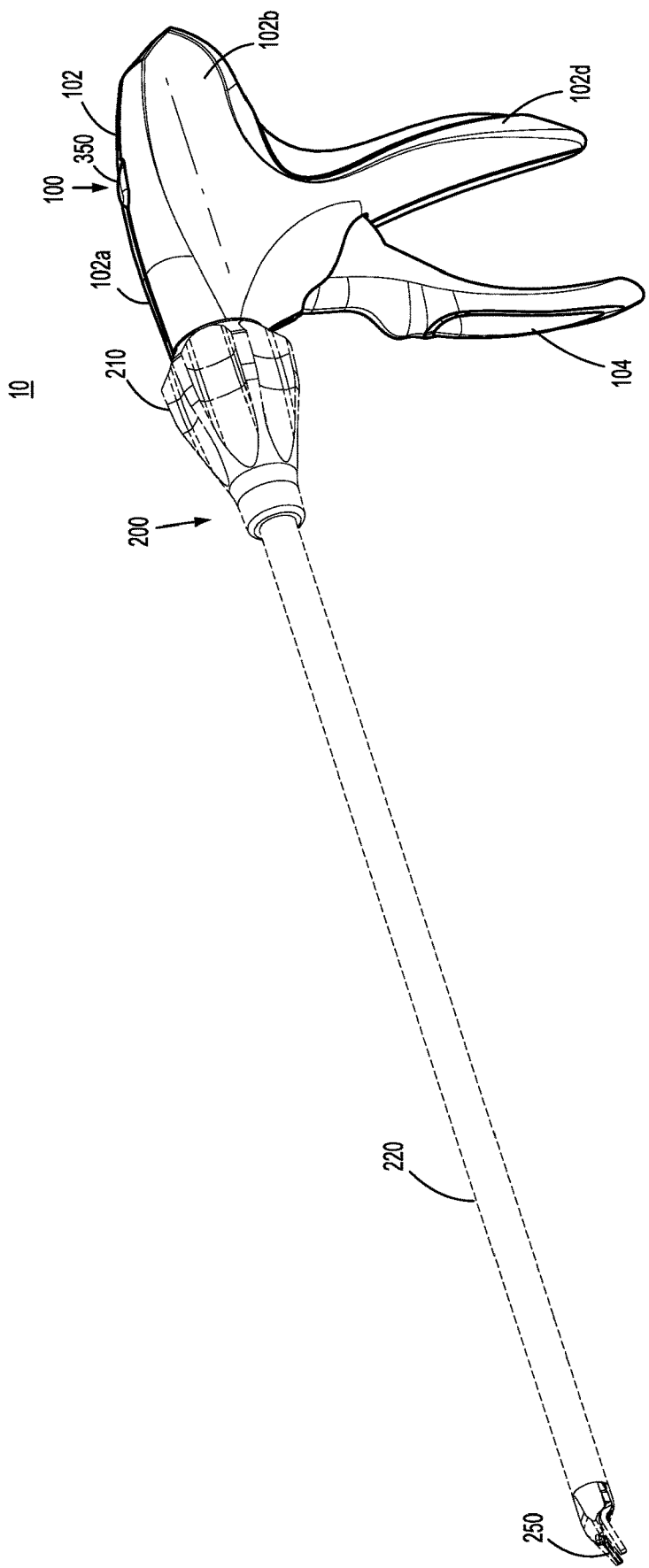
FIG. 1 is a perspective view of an endoscopic surgical clip applier, according to the present disclosure including an endoscopic assembly and a handle assembly.

In accordance with the present disclosure, an endoscopic surgical clip applier includes a ratchet assembly having a first rack, with a first length, operatively associated with a first pawl, a second rack, with a second length less than the first length of the first rack, operatively associated with a second pawl, and a release switch operatively associated with the first pawl. In embodiments, upon actuation of a trigger, the first and second pawls are configured to engage a plurality of first and second rack teeth of the first and second racks, respectively, to prohibit release and reversal of a direction of movement of the trigger until the first and second pawls are disposed within respective clearances of the first and second racks. In embodiments, the release switch is selectively actuatable to move the first pawl out of registration or engagement with the plurality of first rack teeth of the first rack such that the direction of movement of the trigger may be reversed early once the second pawl has traversed the second, lesser length of the second rack. It is contemplated that the release switch may be useful to partially form clips, if desired for example, to secure a catheter around tissue during a cholangiogram or other medical procedure.

Embodiments of endoscopic surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-6, an endoscopic surgical clip applier in accordance with an embodiment of the present disclosure is generally designated as 10. Surgical clip applier 10 generally includes a handle assembly 100 and an endoscopic assembly 200 that extends distally from handle assembly 100. Generally, endoscopic assembly 200 includes a hub assembly 210, a shaft assembly 220 extending from hub assembly 210, and a pair of jaws 250 pivotally connected to a distal end of shaft assembly 220. Optionally, at least one disposable surgical clip cartridge assembly (not shown) may be selectively loadable into shaft assembly 220 of endoscopic assembly 200.

Figure 2A:
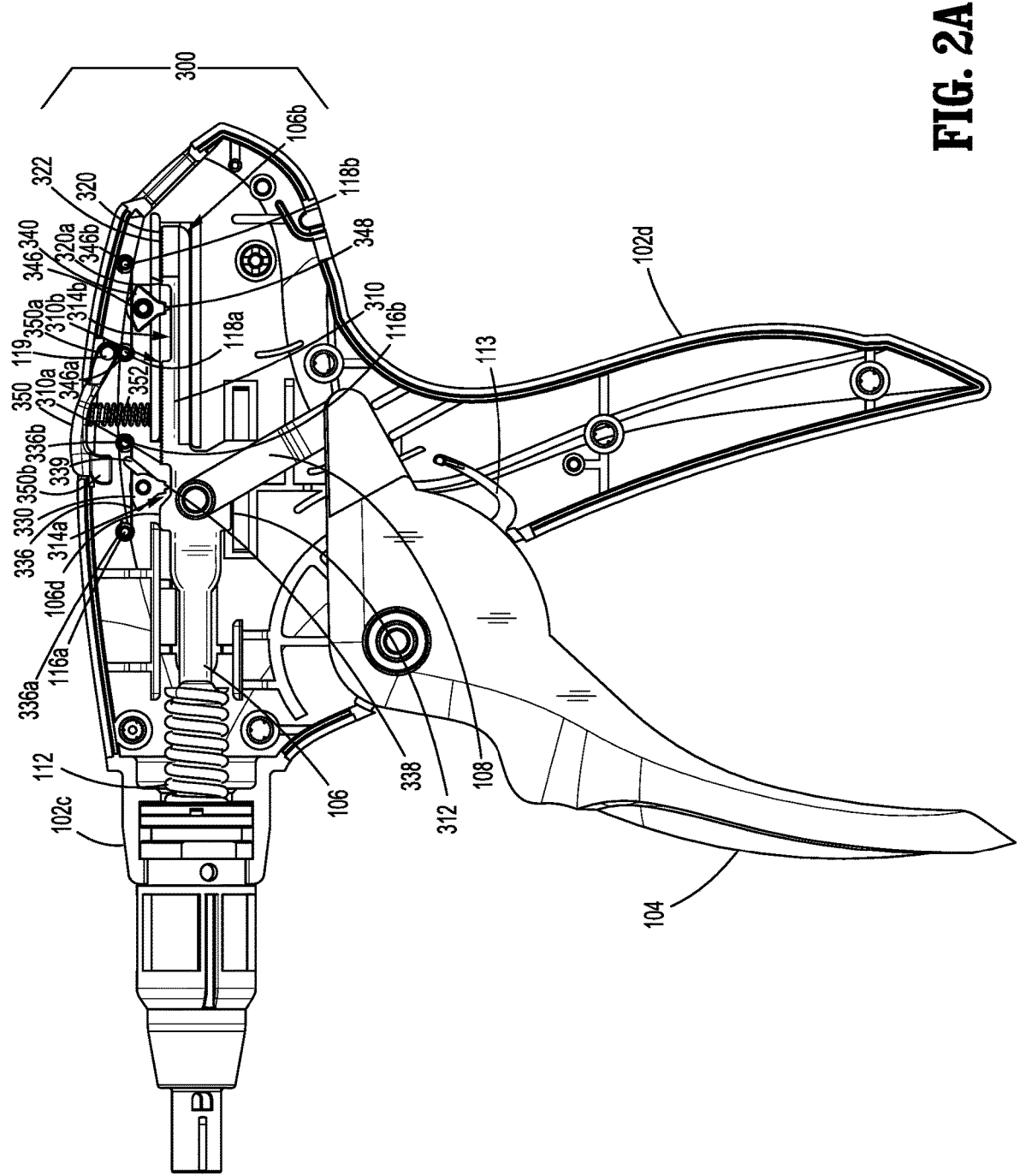
FIG. 2A is a side view, of the handle assembly of FIG. 1 with at least a housing half-section removed therefrom.
Figure 2B:
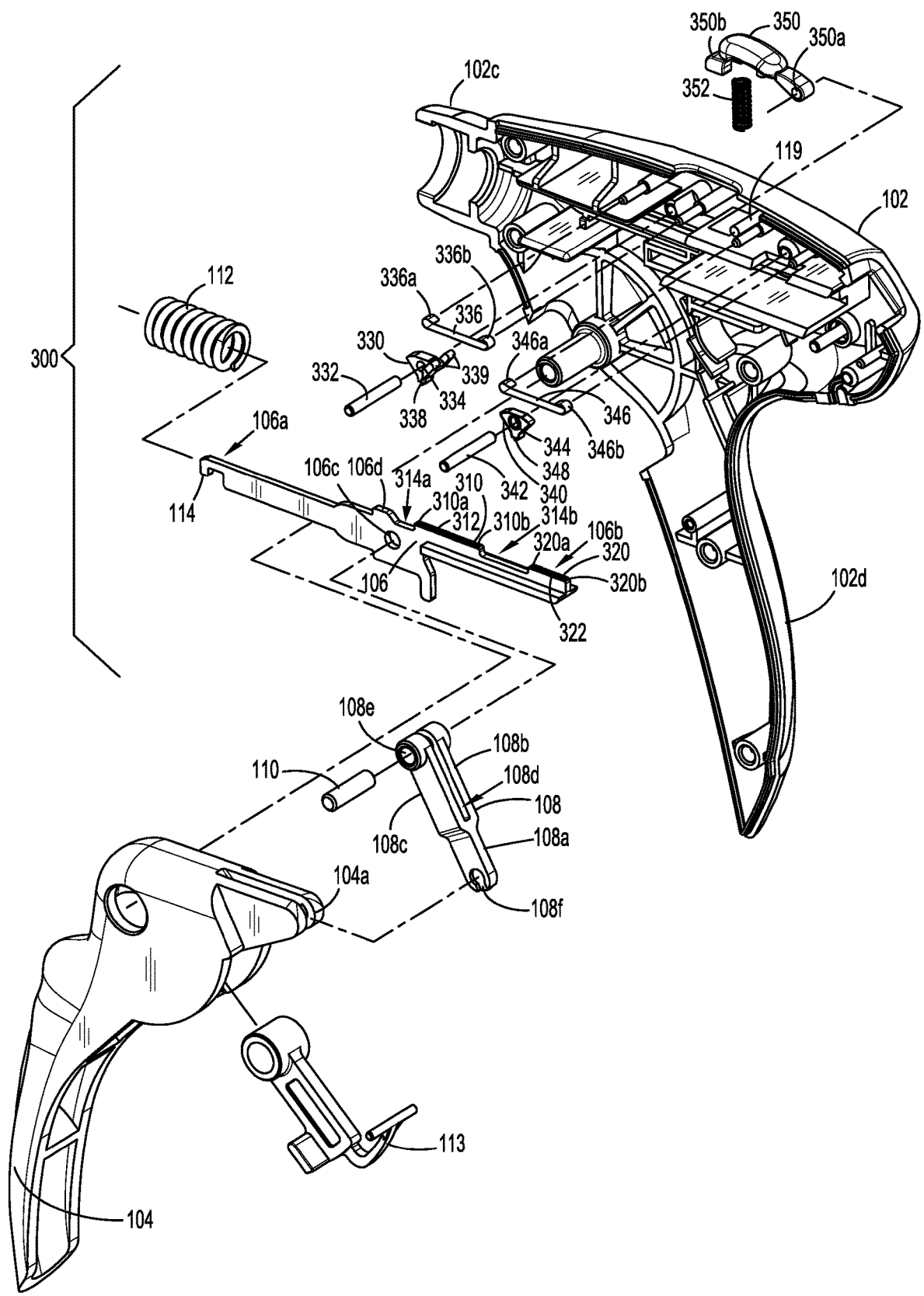
FIG. 2B is a perspective view, with parts separated, of the handle assembly of FIG. 1.

Referring now to FIGS. 1-2B, handle assembly 100 includes a housing 102 having a first or right side half-section 102a and a second or left side half-section 102b. Housing 102 of handle assembly 100 further includes or defines a nose 102c for supporting hub assembly 210 of endoscopic assembly 200, and a fixed handle 102d.

Housing 102 of handle assembly 100 may be formed of a suitable polymer, plastic or thermoplastic material. It is further contemplated that housing 102 of handle assembly 100 may be fabricated from stainless steel or the like.

Handle assembly 100 includes a trigger 104 pivotally supported between right side half-section 102a and left side half-section 102b of housing 102. Trigger 104 is pivotally movable in a first direction such that the trigger 104 and the fixed handle 102d are approximated and pivotably movable in a second, opposite, direction such that the trigger 104 and the fixed handle 102d are spaced-apart.

A drive bar 106 is supported within the housing 102 of the handle assembly 100. The drive bar 106 is a substantially flat member having a distal end portion 106a and a proximal end portion 106b. The distal end portion 106a of drive bar 106 includes a hook member 114 that is provided to mate with a feature of endoscopic assembly 200. The drive bar 106 is operatively coupled to the trigger 104 and the pair of jaws 250 of endoscopic assembly 200 to move the pair of jaws 250 between a spaced-apart configuration and an approximated configuration upon actuation of the trigger 104. Specifically, the handle assembly 100 includes a wishbone link 108 configured to couple the trigger 104 and the drive bar 106. Wishbone link 108 includes a first end portion having a tail 108a and a second end portion having a first arm and a second arm 108b, 108c spaced-apart to define a space 108d therebetween. The tail 108a of the wishbone link 108 is pivotably connected to trigger 104 through a trigger slot 104a. Specifically, tail 108a of wishbone link 108 includes an opening 108f configured for pivotably locating a pin (not specifically shown) defined within trigger slot 104a. The space 108d between the first and second arms 108b, 108c is configured to receive the drive bar 106. The first and second arms 108b, 108c of wishbone link 108, and the drive bar 106 includes corresponding apertures 108e, 106c, respectively, configured to locate a drive bar pin 110 to pivotably connect the wishbone link 108 and the drive bar 106. The wishbone link 108 is configured to translate the pivotal movement of the trigger 104 into longitudinal movement of the drive bar 106, as will be detailed below.

The drive bar 106 is configured to move one or more driving structures to load, and actuate the pair of jaws 250 to form a clip 290 (see FIG. 6) fully or partially, and then reset to an initial position for the next clip application. To achieve this, a biasing member, such as, for example, a first return spring 112 is disposed to surround the drive bar 106 adjacent the distal end portion 106a such that, after the trigger 104 is actuated and the wishbone link 108 advances the drive bar 106 in a longitudinal or distal manner, the first return spring 112 is provided to return the drive bar 106 and the trigger 104 to its original position for the next clip application. Further, in one embodiment, a second return spring 113 is disposed in housing 102 of handle assembly 100 and configured to operatively connect the trigger 104 and the fixed handle 102d such that, after the trigger 104 is actuated, the second return spring 113 is provided to return the trigger 104 to its original position.

With continued reference to FIGS. 2A and 2B, surgical clip applier 10 includes a ratchet assembly 300 disposed within housing 102 of handle assembly 100. The ratchet assembly 300 generally includes a first rack 310, a second rack 320, a first pawl 330, a second pawl 340, and a release switch 350 at least partially supported within housing 102 of handle assembly 100.

As shown in FIGS. 2A and 2B, the first and second racks 310, 320 are supported by or are provided on a top surface 106d of the drive bar 106. The first rack 310 includes a distal end 310a and a proximal end 310b. The first rack 310 defines a plurality of first rack teeth 312 in series between the distal end 310a and the proximal end 310b thereof. Similarly, the second rack 320 includes a distal end 320a and a proximal end 320b. The second rack 320 defines a plurality of second rack teeth 322 in series between the distal end 320a and the proximal end 320b thereof.

The top surface 106d of the drive bar 106 also includes a distal clearance or well 314a located adjacent the distal end 310a of the first rack 310 and a proximal clearance or well 314b located between the proximal end 310b of the first rack 310 and the distal end 320a of the second rack 320. The distal well 314a is configured to receive the first pawl 330 and the proximal well 314b is configured to receive the second pawl 340 in an initial and/or reset position, as will be detailed further.

As shown in FIG. 2B, the first and second pawls 330, 340 are pivotably mounted within the handle assembly 100 between the right side half-section 102a and the left side half-section 102b of the housing 102. Specifically, the first pawl 330 is pivotably mounted within the handle assembly 100 between the right side half-section 102a and the left side half-section 102b of the housing 102 by a first pawl pin 332 at a location wherein the first pawl 330 is in substantial operative engagement with the first rack 310. The first pawl pin 332 extends through a slot 334 defined in the first pawl 330. Similarly, the second pawl 340 is pivotably mounted within the handle assembly 100 between the right side half-section 102a and the left side half-section 102b of the housing 102 by a second pawl pin 342 at a location wherein the second pawl 340 is in substantial operative engagement with the second rack 320. The second pawl pin 342 extends through a slot 344 defined in the second pawl 340.

As shown in FIGS. 2A and 2B, the ratchet assembly 300 further includes a first pawl spring 336 configured to vertically bias the first pawl 330 into operative engagement with the first rack 310 and a second pawl spring 346 configured to vertically bias the second pawl 340 into operative engagement with the second rack 320. The first pawl spring 336 includes a distal hook 336a and a proximal hook 336b configured to latch onto a first set of support pins 116a, 116b of housing 102, respectively, and the second pawl spring 346 includes a distal hook 346a and a proximal hook 346b configured to latch onto a second set of support pins 118a, 118b of housing 102, respectively. It is contemplated that the first and second pawl springs 336, 346 are positioned in a manner configured to maintain a first pawl tooth 338 of the first pawl 330 and a second pawl tooth 348 of the second pawl 340 in registration or engagement with the plurality of first and second rack teeth 312, 322, respectively, as well as to maintain the first and second pawls 330, 340 in a rotated or canted position.

With continued reference to FIGS. 2A and 2B, ratchet assembly 300 further includes release switch 350 at least partially supported within housing 102 of handle assembly 100. In embodiments, release switch 350 includes a slot 350a on a proximal end portion thereof configured for locating a mounting pin 119 of housing 102 such that, the release switch 350 is pivotable thereabout. Release switch 350 is operatively associated with the first pawl 330 and includes an engagement member 350b on a distal end portion thereof that is operable to engage the first pawl 330 to selectively move the first pawl 330, out of operative registration or engagement with the plurality of first rack teeth 312 of the first rack 310, as will be detailed further. In other embodiments, release switch 350 may include various configurations suitable for its intended purpose and may be any ergonomic shape configured to provide access to a user during operation.

In embodiments, the first pawl 330 includes a lockout member 339 extending therefrom and provided to selectively engage the engagement member 350b of release switch 350 to prevent the release switch 350 from moving the first pawl tooth 338 of the first pawl 300 out of registration or engagement with the plurality of first rack teeth 312 of the first rack 310.

Ratchet assembly 300 further includes a release spring 352 supported in housing 102 of handle assembly 100 and operatively associated with the release switch 350 to return the release switch 350 to its un-actuated, home position where the release switch 350 is disengaged from the first pawl 330. It is contemplated that release spring 352 may include any suitable biasing member, such as, for example, a compression spring, a leaf spring, or deforming member extending from release switch 350.

Figure 3A:
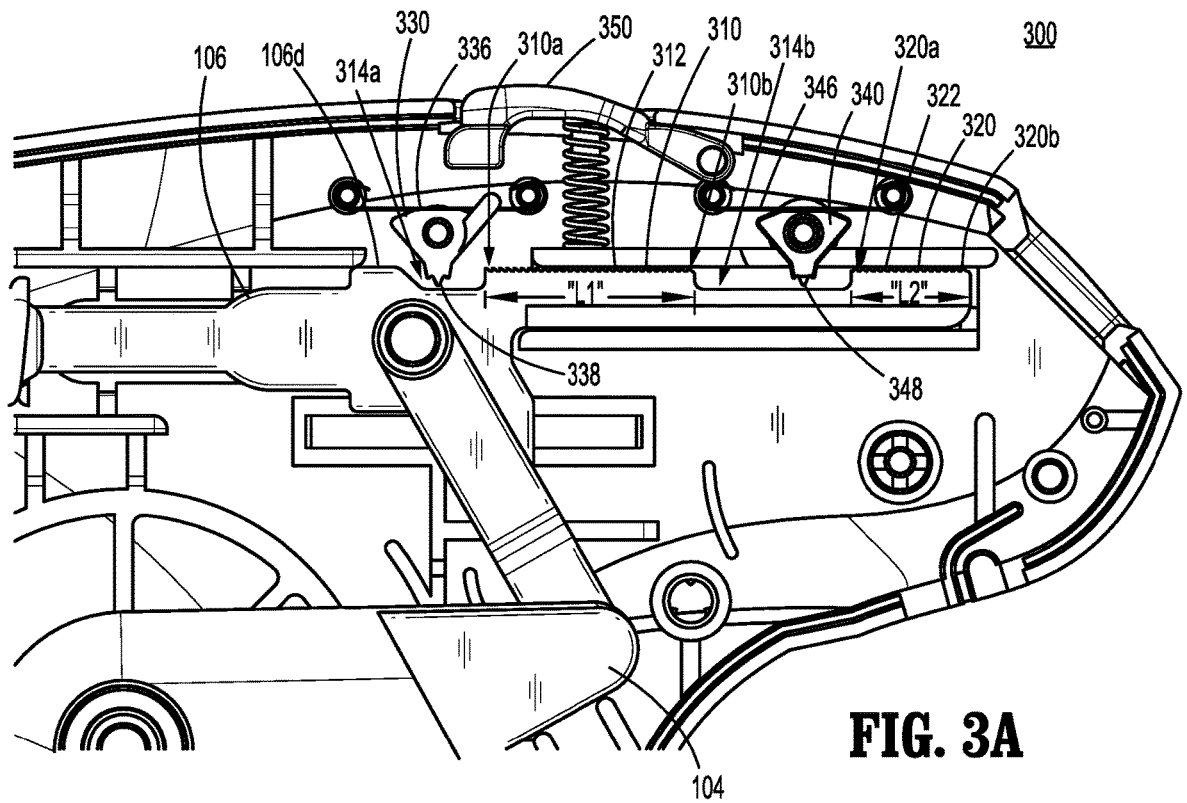
FIG. 3A is a side view, of the handle assembly of FIG. 2A, illustrating a ratchet assembly thereof, in an initial/reset position of a normal actuation of the ratchet assembly.

With brief reference to FIG. 3A, in the initial and/or reset position, the first pawl 330 is disposed within distal well 314a and the second pawl 340 is disposed within proximal well 314b.

Figure 3B:
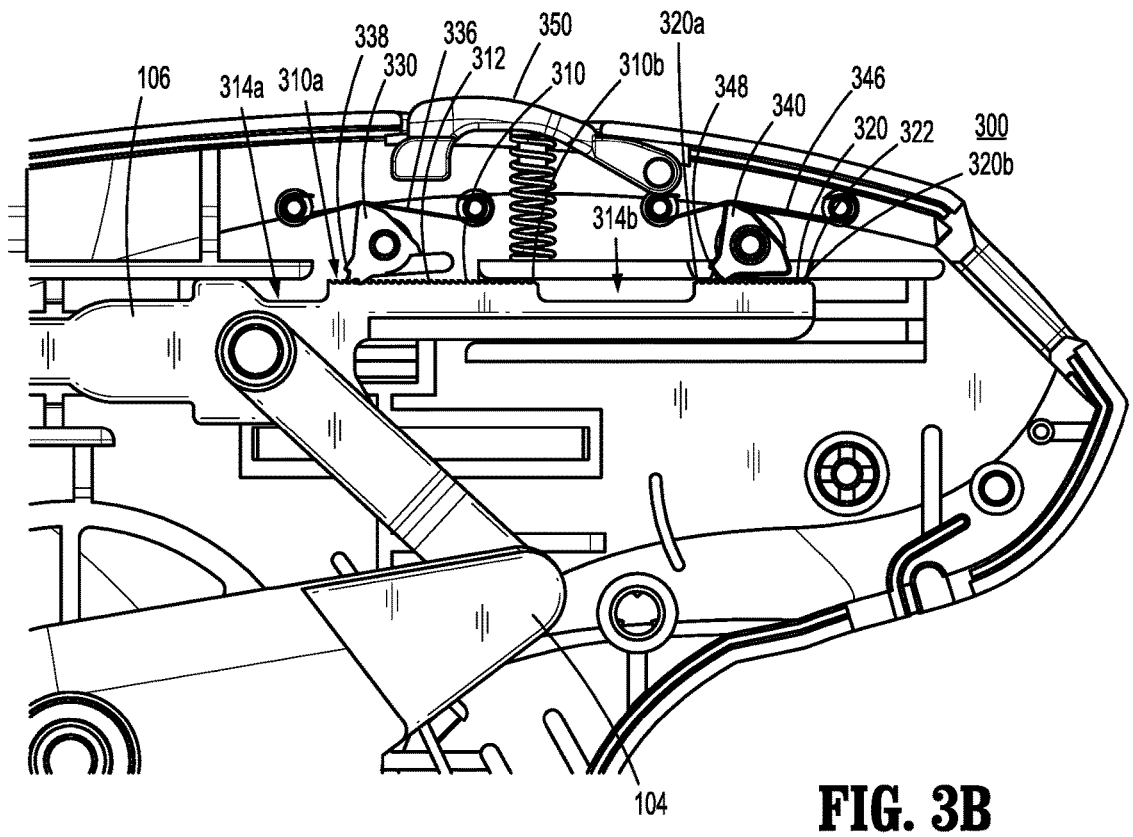
FIG. 3B is a side view, of the handle assembly of FIG. 2A, illustrating the ratchet assembly of FIG. 3A, in a first configuration of the normal actuation of the ratchet assembly.
Figure 3C:
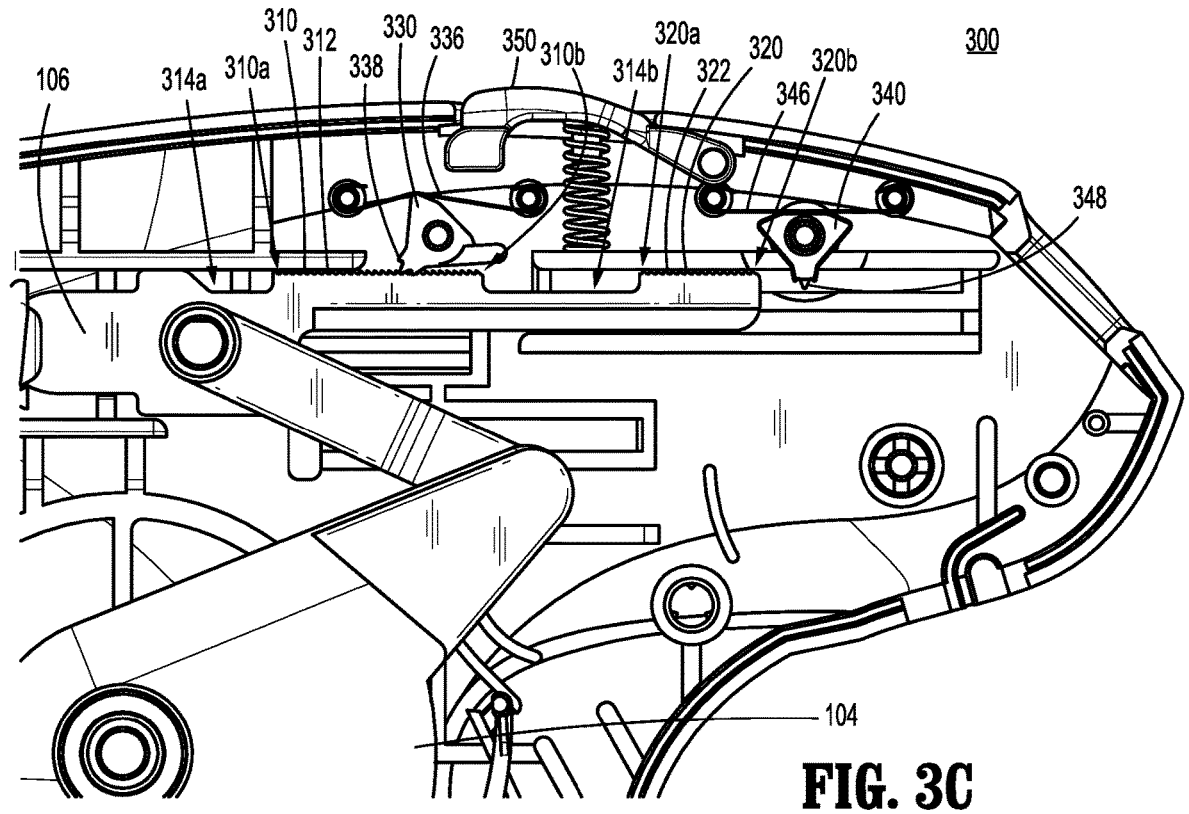
FIG. 3C is a side view, of the handle assembly of FIG. 2A, illustrating the ratchet assembly of FIG. 3A, in a second configuration of the normal actuation of the ratchet assembly.
Figure 3D:
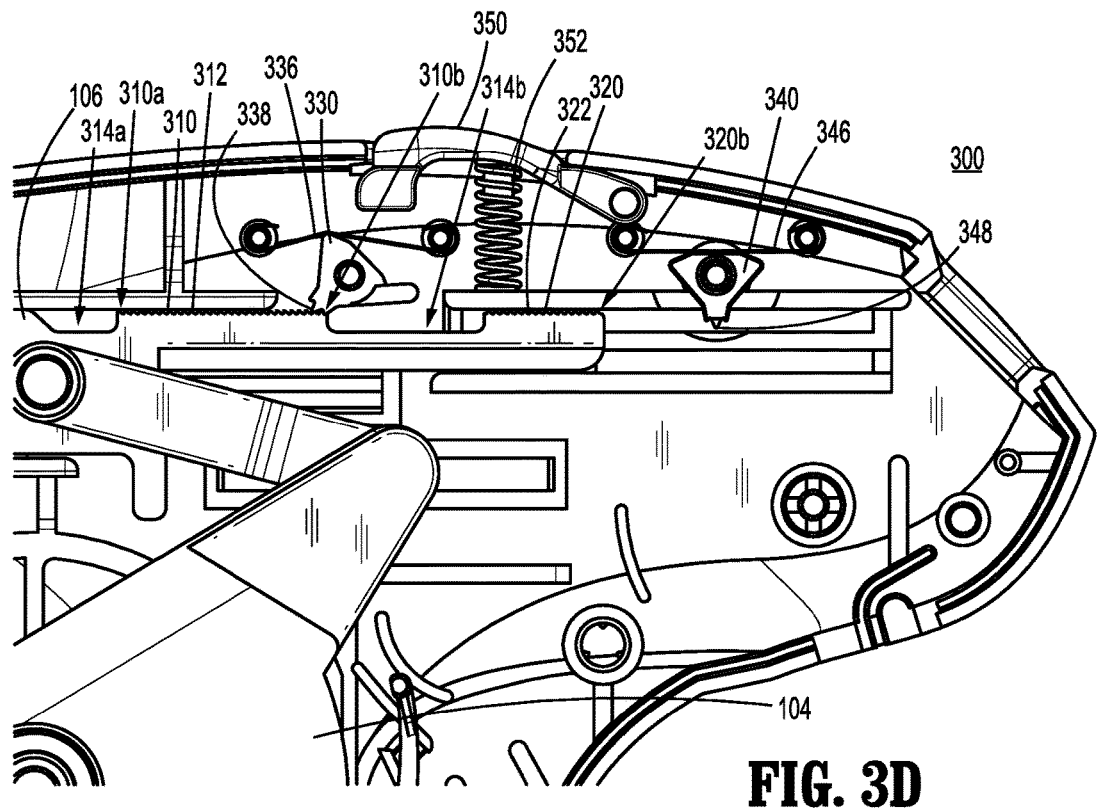
FIG. 3D is a side view, of the handle assembly of FIG. 2A, illustrating the ratchet assembly of FIG. 3A, in a third configuration of the normal actuation of the ratchet assembly.

With continued reference to FIG. 3A and additional reference to FIGS. 3B-3D, a normal actuation of ratchet assembly 300 is disclosed. In use, as trigger 104 is actuated, from a fully un-actuated position, the plurality of first and second rack teeth 312, 322 of the first and second racks 310, 320, respectively, are moved to a first position, into registration or engagement with first pawl tooth 338 and second pawl tooth 348 of the first and second pawls 330, 340, respectively (see FIG. 3B).

First rack 310 has a first length "L1" (see FIG. 3A) which allows the first pawl 330 to reverse over the first rack 310 (from the distal well 314a; see FIG. 3A) as the first rack 310 moves in a distal direction relative to the pair of jaws 250 (see FIG. 1), as trigger 104 reaches a fully actuated position, and advance back over the first rack 310 (from the proximal end 310b of the first rack 310; see FIG. 3D), when the first rack 310 moves in a proximal direction relative to the pair of jaws 250, as trigger 104 reaches a fully un-actuated position. The first length "L1" of first rack 310 defines a full stroke length of trigger 104, drive bar 106 or handle assembly 100 (see FIG. 1), where a clip 290 has been fully formed and fired from surgical clip applier 10.

Second rack 320 has a second length "L2," (see FIG. 3A) which is less than the first length "L1" of first rack 310. The second length "L2" allows the second pawl 340 to reverse over the second rack 320 (from the proximal well 314b; see FIG. 3A) as the second rack 320 moves in the distal direction relative to the pair of jaws 250 (see FIG. 1), as trigger 104 reaches a partially actuated position, and advance back over the second rack 320 (from a position that is proximal of the proximal end 320b of the second rack 320; see FIG. 3D), when the second rack 320 moves in a proximal direction relative to the pair of jaws 250, as trigger 104 reaches a fully un-actuated position. The second length "L2" of second rack 320 defines a partial stroke length of trigger 104, drive bar 106 or handle assembly 100 (see FIG. 1), where a clip 290 has been partially formed, or formed enough to be fired from surgical clip applier 10 and a new clip 290 loaded into the pair of jaws 250 without an inadvertent double loading of clips 290 into the pair of jaws 250. It is contemplated that in the normal actuation of ratchet assembly 300, the first and second pawls 330, 340 and the respective first and second racks 310, 320 cooperate such that the stroke length of trigger 104, drive bar 106 or handle assembly 100 is determined by the greater first length "L1" of first rack 310 to achieve a fully formed clip 290 being fired from surgical clip applier 10.

Figure 4A:
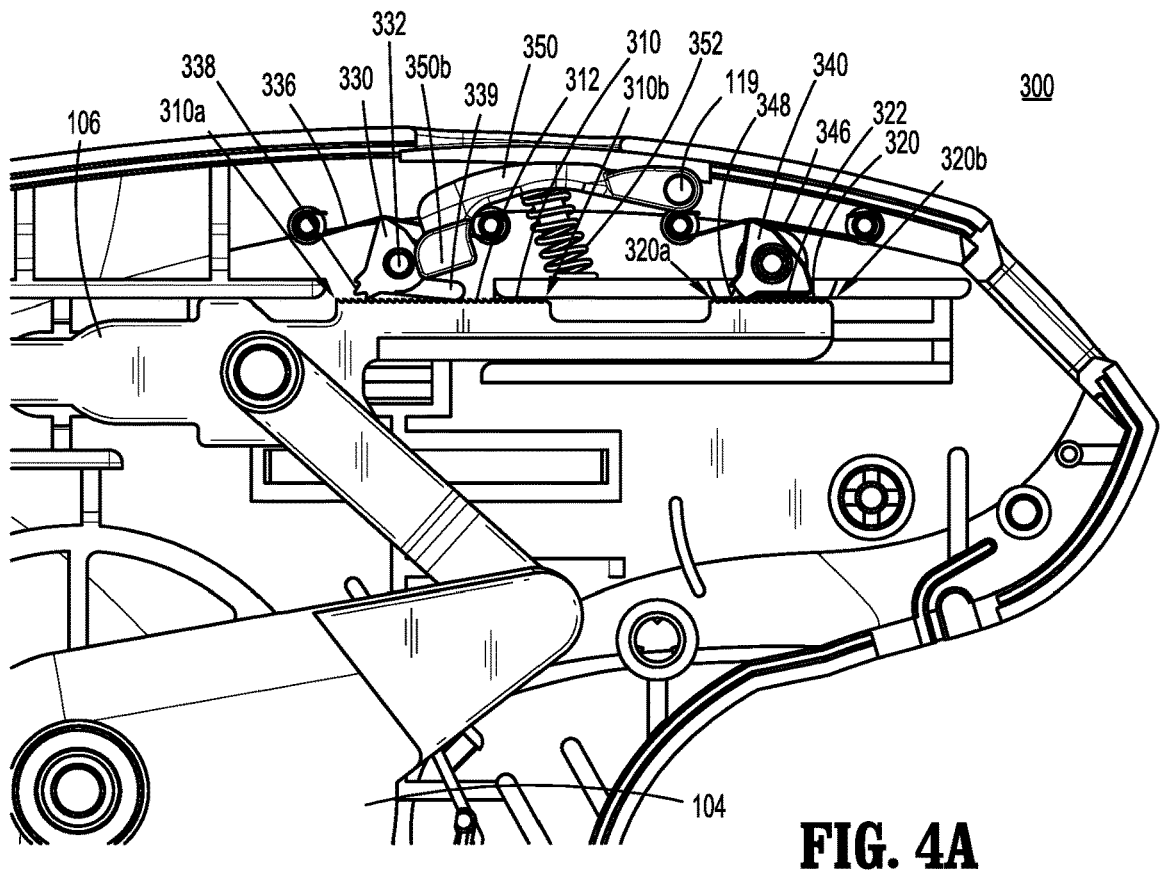
FIG. 4A is a side view, of the handle assembly of FIG. 2A, illustrating the ratchet assembly thereof, in a first configuration of a partial actuation of the ratchet assembly.
Figure 4B:
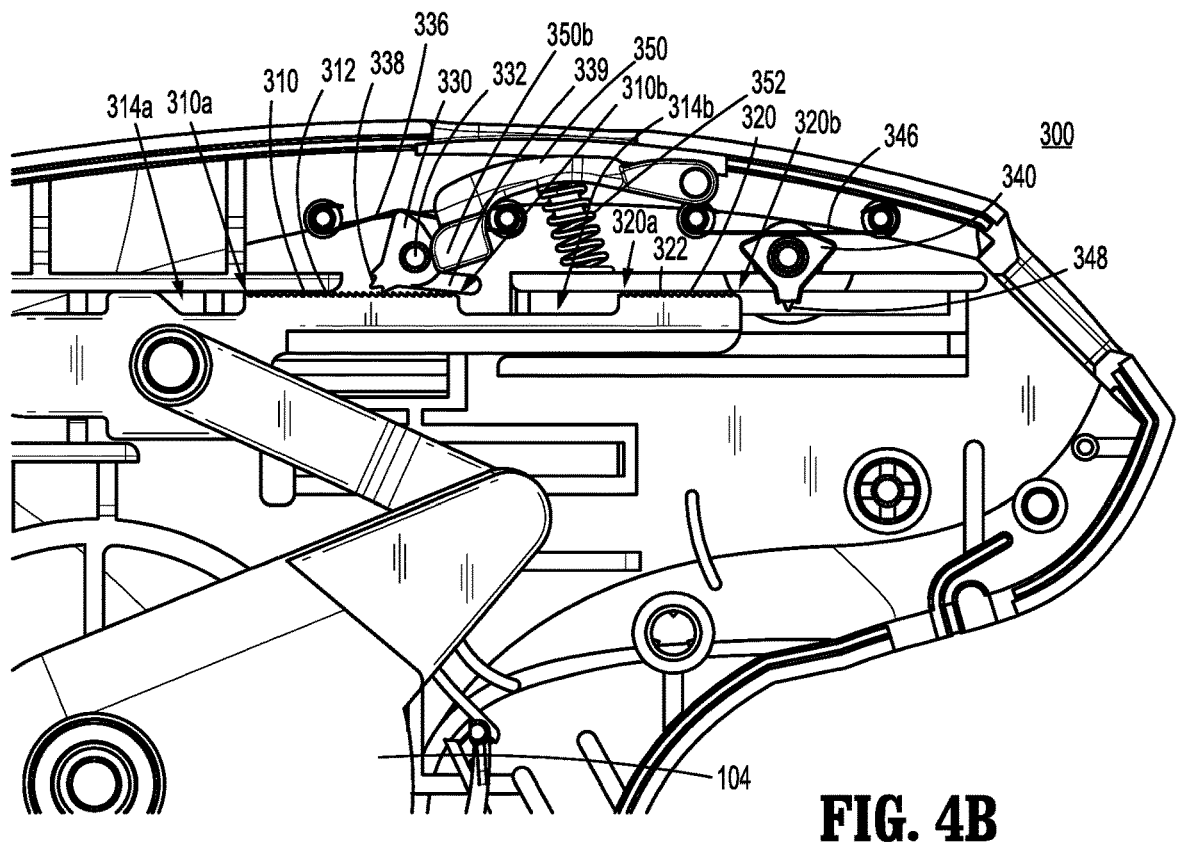
FIG. 4B is a side view, of the handle assembly of FIG. 2A, illustrating the ratchet assembly of FIG. 4A, in a second configuration of the partial actuation of the ratchet assembly.
Figure 4C:
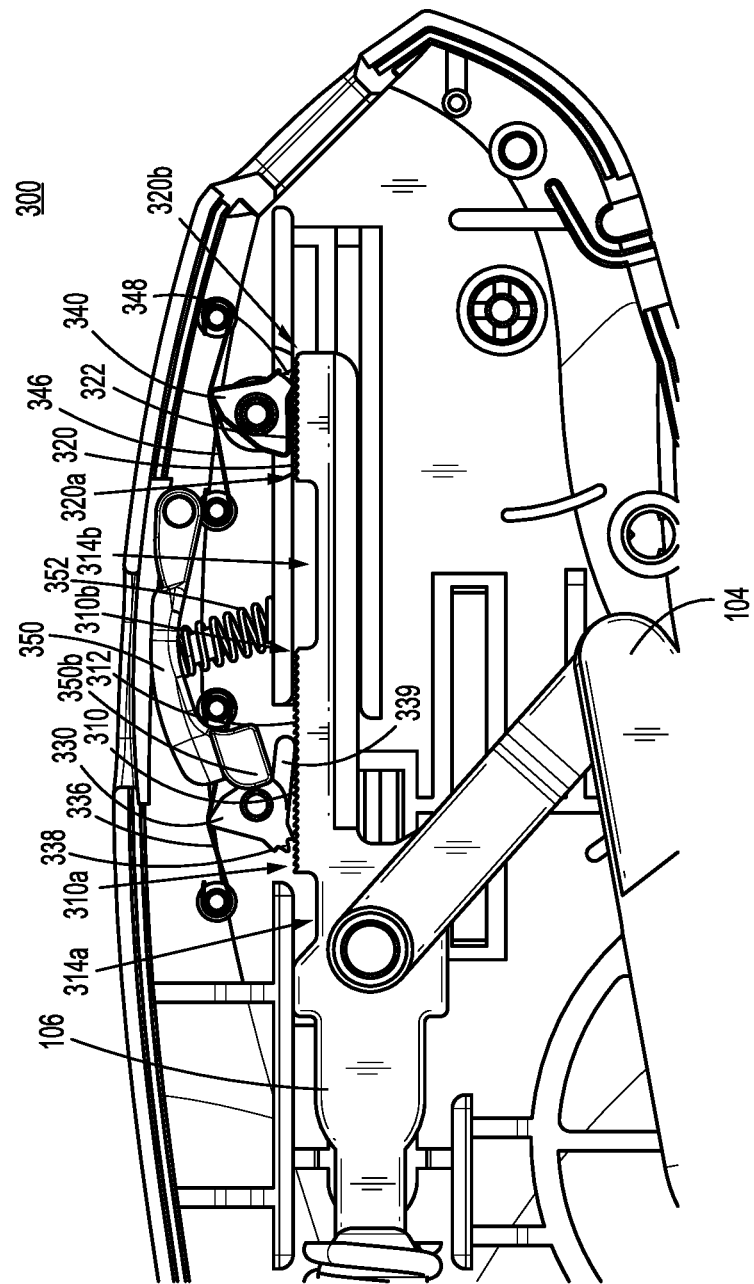
FIG. 4C is a side view, of the handle assembly of FIG. 2A, illustrating the ratchet assembly of FIG. 4A, in a third configuration of the partial actuation of the ratchet assembly.

Referring now to FIGS. 4A-4C, a partial actuation of ratchet assembly 300 is disclosed. It is contemplated that a partial actuation of ratchet assembly 300 may enable a user to fire a partially formed clip 290 from surgical clip applier 10 when performing a cholangiogram procedure or the like. It is also contemplated that a partial actuation of ratchet assembly 300 may enable a user to abort a firing of a clip 290 from surgical clip applier 10 if the clip 290 is inadvertently positioned in a wrong location or if a clip 290 is positioned over an obstruction.

In use, with reference to FIG. 4A, after trigger 104 is actuated such that, the plurality of first and second rack teeth 312, 322 of the first and second racks 310, 320, respectively, are moved to the first position, into registration or engagement with first pawl tooth 338 and second pawl tooth 348 of the first and second pawls 330, 340, respectively (see FIG.

3B), release switch 350 is actuated such that release switch 350 pivots about mounting pin 119 of housing 102 and engagement member 350b engages the first pawl 330 to rotate the first pawl 330 about first pawl pin 332. In this manner, the first pawl 330 is moved to a second position, out of registration or engagement with the plurality of first rack teeth 312 of the first rack 310. As shown in FIG. 4A, though release switch 350 is actuated to move the first pawl 330 to the second position, second pawl 340 remains in the first position until the second pawl 340 is moved to a position proximal of the proximal end 320b of the second rack 320 to clear the second rack 320, as shown in FIG. 4B. With first pawl 330 out of registration or engagement with the first rack 310, the stroke length of trigger 104, drive bar 106 or handle assembly 100 is determined by the lesser second length "L2" of second rack 320 (relative to first length "L1" of first rack 310). The engagement between second pawl 340 and second rack 320 for a duration of the lesser second length "L2" prevents an inadvertent return of trigger 104 during a specific portion of the stroke until, a clip 290 loaded into the pair of jaws 250 is partially formed, enough to be fired from surgical clip applier 10, such that a new clip 290 may be loaded into the pair of jaws 250 without an inadvertent double loading of clips 290 into the pair of jaws 250.

Referring now to FIG. 4C, with release switch 350 still actuated to engage first pawl 330, trigger 104 may be returned to a fully un-actuated position (from its partially actuated position), once second pawl 340 advances back over the second rack 320 and is disposed within the proximal well 314b to complete the partial actuation of ratchet assembly 300. Release switch 350 may then be released such that the release switch 350 is returned to its original position under the bias of release spring 352 and first pawl 330 is disposed within distal well 314a (see FIG. 3A).

In embodiments, it is contemplated that if release switch 350 is released during a portion of the partial actuation of ratchet assembly 300 (for example, see FIG. 4A), such that engagement member 350b of release switch 350 is disengaged from first pawl 330, first pawl spring 336 is provided to return first pawl 330 to the first position, such that the plurality of first rack teeth 312 of the first rack 310 are moved into registration or engagement with first pawl tooth 338 of the first pawl 330. Accordingly, surgical clip applier 10 is returned to the normal actuation of ratchet assembly 300 (see FIGS. 3A-3D), where the stroke length of trigger 104, drive bar 106 or handle assembly 100 is determined by the greater first length "L1" of first rack 310 (relative to second length "L2" of second rack 320) to achieve a fully formed clip 290 being fired from surgical clip applier 10. This feature may be advantageous in instances, such as, for example, where release switch 350 is inadvertently actuated.

Figure 5A:
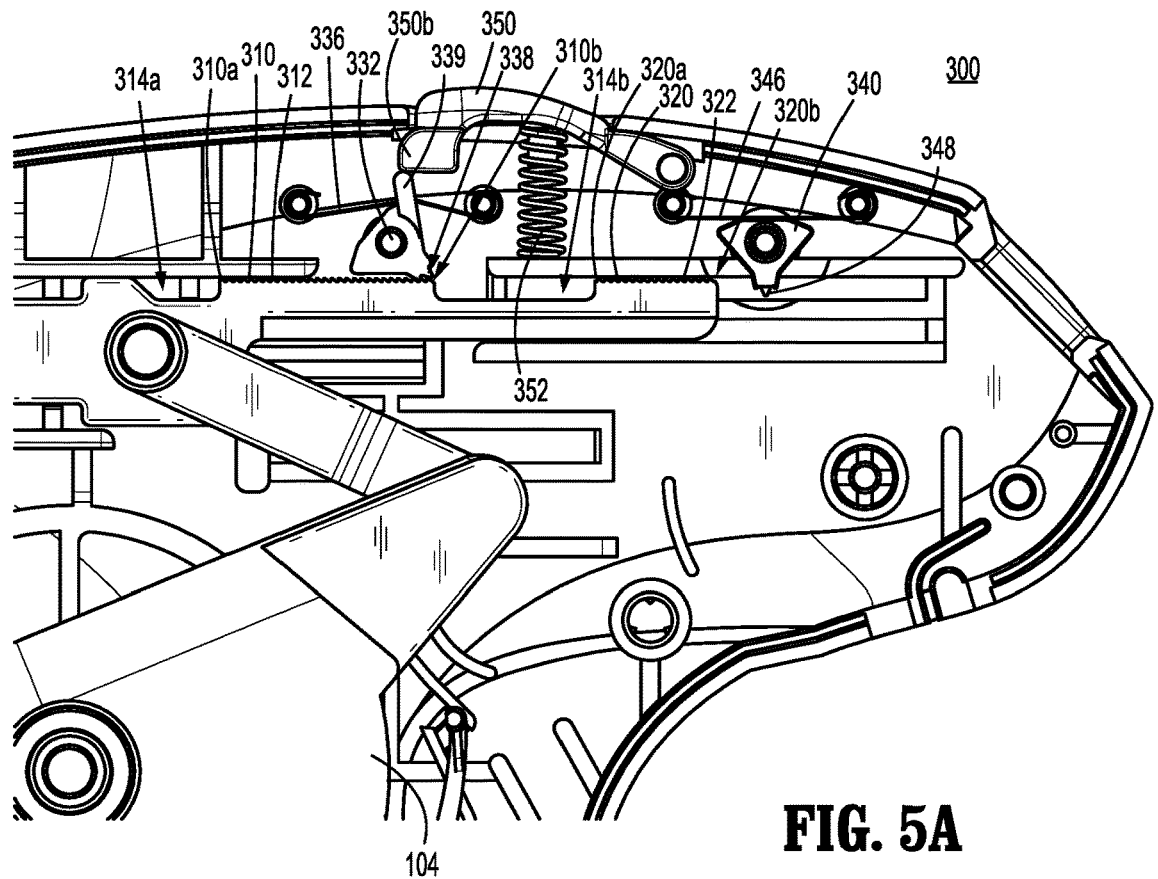
FIG. 5A is a side view, of the handle assembly of FIG. 2A, illustrating the ratchet assembly thereof, in a first configuration of a return stroke of the normal actuation of ratchet assembly.
Figure 5B:
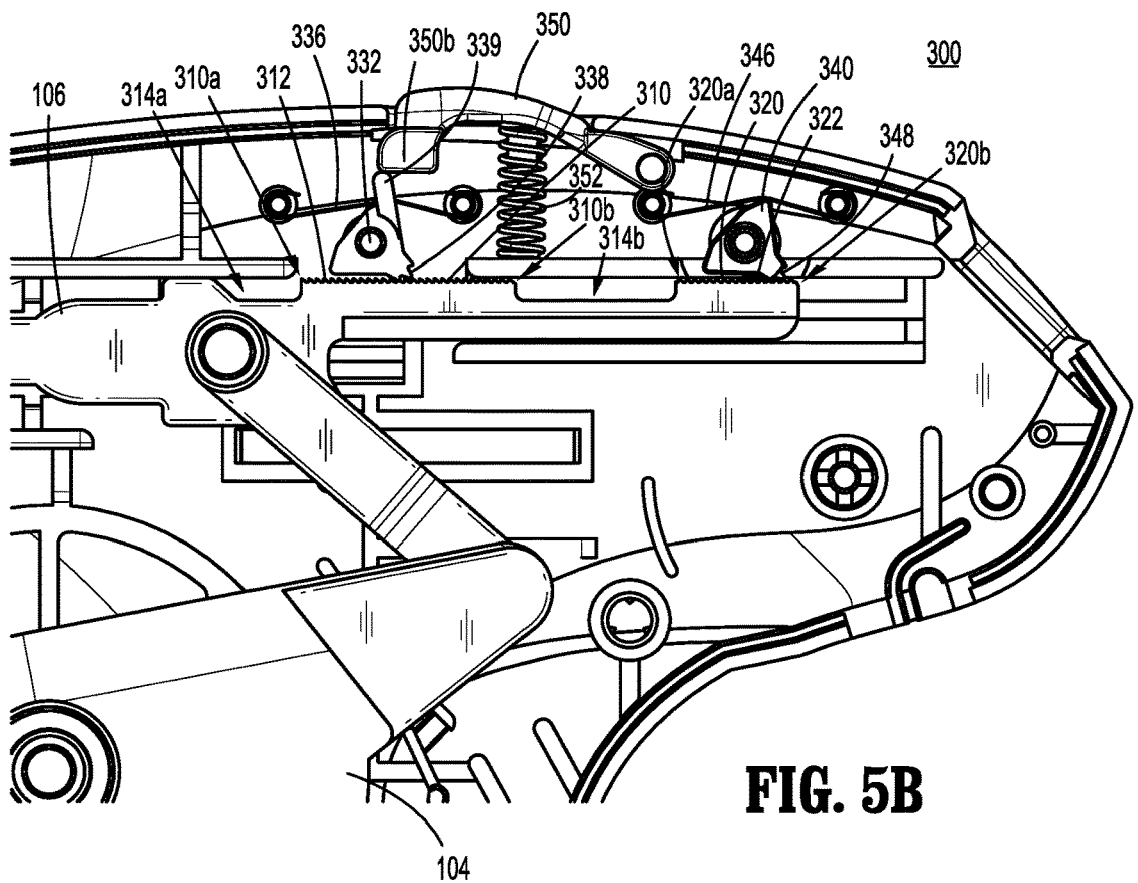
FIG. 5B is a side view, of the handle assembly of FIG. 2A, illustrating the ratchet assembly of FIG. 5A, in a second configuration of the return stroke of the normal actuation of ratchet assembly.
Figure 5C:
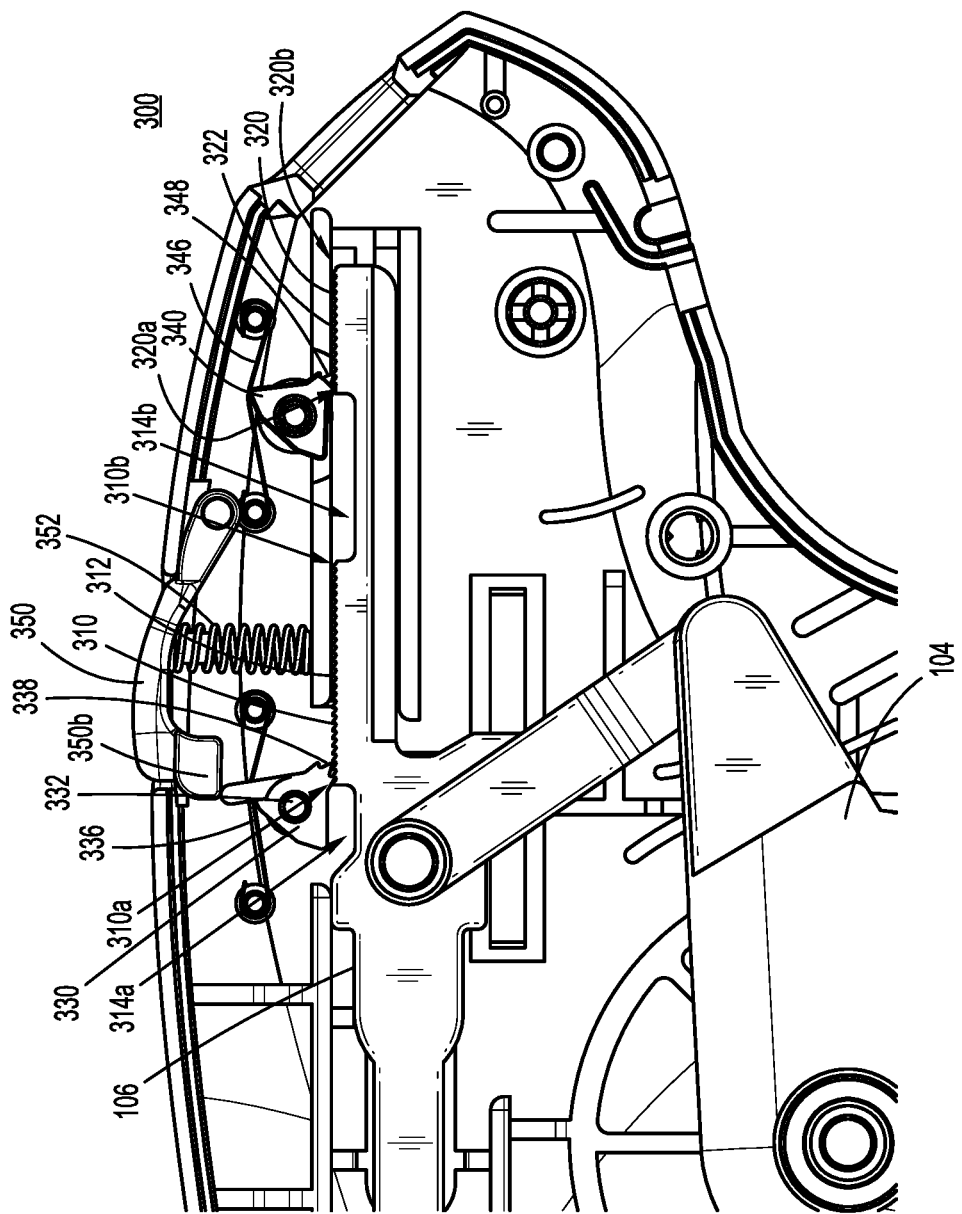
FIG. 5C is a side view, of the handle assembly of FIG. 2A, illustrating the ratchet assembly of FIG. 5A, in a third configuration of the return stroke of the normal actuation of ratchet assembly.
Figure 6:
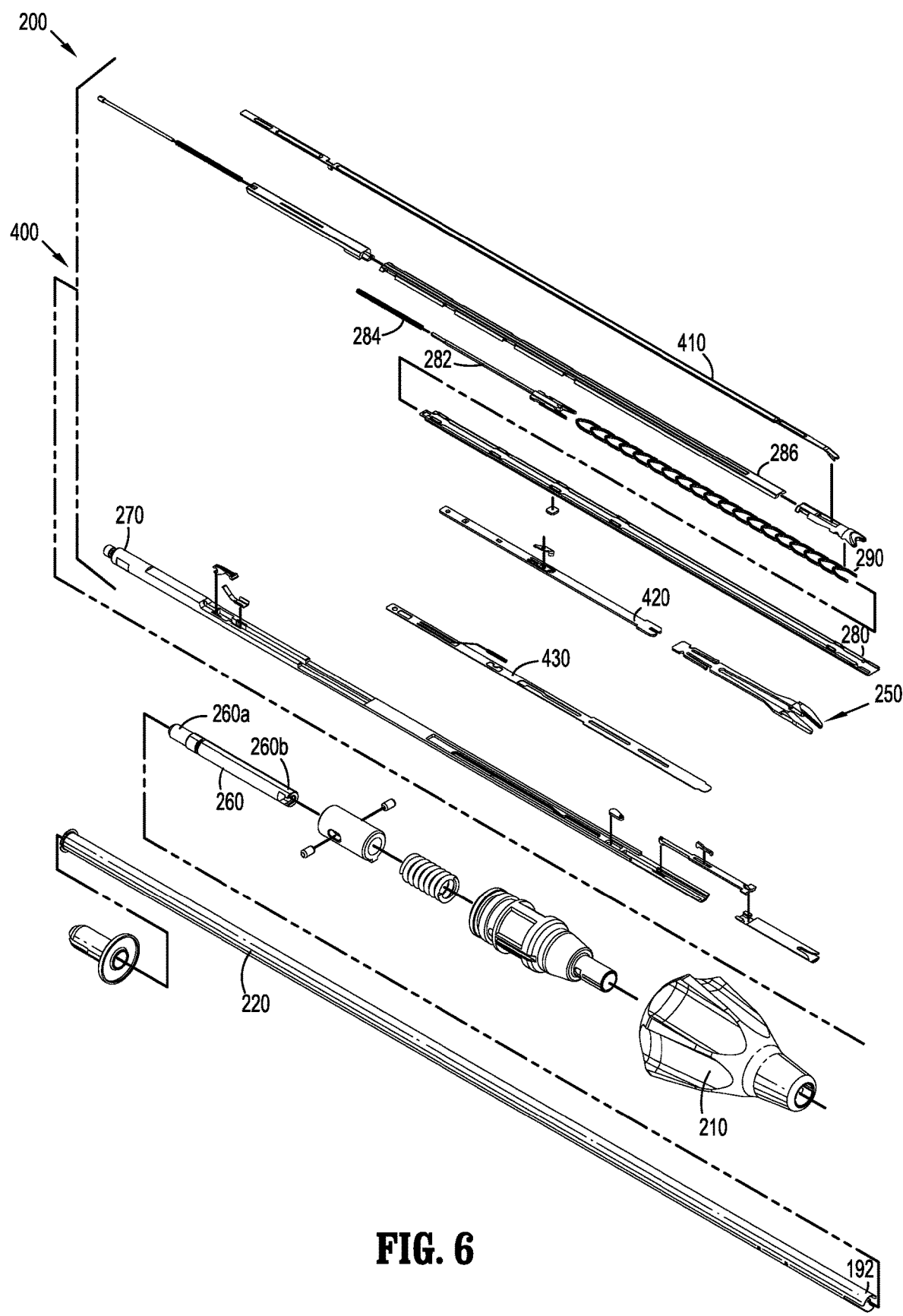
FIG. 6 is a perspective view of the endoscopic assembly of FIG. 1, with parts separated.

Referring now to FIGS. 5A-5C, a return stroke of the normal actuation of ratchet assembly 300 is disclosed. With trigger 104 in the fully actuated position such that first pawl 330 is disposed at proximal end 310b of first rack 310 and second pawl 340 is disposed at a position proximal of the proximal end 320b of the second rack 320 (see FIG. 5A), trigger 104 is released such that first and second racks 310, 320 are moved in the proximal direction relative to the pair of jaws 250. Concomitantly, first and second pawls 330, 340 are advanced over first and second racks 310, 320, respectively, such that the plurality of first and second rack teeth 312, 322 of the first and second racks 310, 320, respectively, are moved to the first position, into registration or engagement with first pawl tooth 338 and second pawl tooth 348 of the first and second pawls 330, 340, respectively (see FIG. 5B). During the return stroke, first pawl 330 is rotated about first pawl pin 332 such that lockout member 339 of first pawl 330 is positioned to engage the engagement member 350b of release switch 350, if release switch 350 is actuated. In this manner, the registration or engagement between the first pawl tooth 338 of first pawl 330 with the plurality of first rack teeth 312 of the first rack 310 cooperates with lockout member 339 of first pawl 330 to prevent the release switch 350 from engaging the first pawl 330 to rotate or move the first pawl tooth 338 of the first pawl 300 out of registration or engagement with the plurality of first rack teeth 312 of the first rack 310. It is contemplated that such a feature ensures that trigger 104 is moved to the fully un-actuated position, a new clip 290 is loaded into the pair of jaws 250, and ratchet assembly 300 is moved to the initial and/or reset position, where the first pawl 330 is disposed within distal well 314a and the second pawl 340 is disposed within proximal well 314b (see FIG. 3A).

Though the figures of the present disclosure illustrate configurations where the first and second racks 310, 320 are longitudinally aligned on drive bar 106, with release switch 350 being selectively engageable with first pawl 330, it is contemplated that the first and second racks 310, 320 may include configurations where the first and second racks 310, 320 are reversed, stacked, side-by-side, or a combination thereof. Further, it is contemplated that release switch 350 may be selectively engageable with second pawl 340. In addition, it is contemplated that actuating release switch 350 may emit audible and/or tactile feedback to the user.

As noted above, and illustrated in FIG. 6, surgical clip applier 10 includes an endoscopic assembly 200 having hub assembly 210, shaft assembly 220, and the pair of jaws 250. Hub assembly 210 is rotatably mounted on nose 102c (see FIG. 2A) of housing 102 of handle assembly 100 and is connected to a proximal end portion of shaft assembly 220 to provide a three hundred sixty degree rotation of the shaft assembly 220 and the pair of jaws 250 thereon relative to a longitudinal center axis of shaft assembly 220. Hub assembly 210 has a suitable configuration so as to be rotated simply using a clinician's finger.

Endoscopic assembly 200 includes a spindle link 260 for operatively connecting drive bar 106 to a driving mechanism 400 to move the pair of jaws 250 between the spaced-apart configuration and the approximated configuration upon actuation of trigger 104. Specifically, hook member 114 (see FIG. 2B) of drive bar 106 is coupled to a first end 260a of spindle link 260 and a spindle 270 of drive mechanism 400 is coupled to a second end 260b of spindle link 260. In this manner, translation of drive bar 106 in a distal and proximal direction can thus advance and retract spindle 270, respectively.

Drive mechanism 400 further includes an elongated clip channel member 280 for retaining a number of surgical clips 290 shown in an aligned manner above the clip channel member 280. A clip follower 282 and a clip follower spring 284 are provided to urge the surgical clips 290 distally through the elongated clip channel member 280. A channel cover 286 is provided to overlay the elongated clip channel member 280 and retain and guide the clip follower 282 and clip follower spring 284 and the surgical clips 290 distally in the elongated clip channel member 280.

Drive mechanism 400 also has a feed bar 410 for feeding the surgical clips 290 between the pair of jaws 250. Drive mechanism 400 also includes a filler component 420 and a wedge plate 430.

For a more detailed description of the construction and operation of endoscopic assembly 200, reference may be made to U.S. Pat. No. 7,637,917, the entire content of which is incorporated herein by reference.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An endoscopic surgical clip applier, comprising:
   an endoscopic assembly including:
      a shaft assembly; and
      a pair of jaw members operatively coupled to, and extending from the shaft assembly; and
   a handle assembly including:
      a housing selectively connectable to the endoscopic assembly;
      a fixed handle extending from the housing;
      a trigger pivotally connected to the fixed handle;
      a drive bar disposed within the housing of the handle assembly and operatively coupled to the trigger and the pair of jaw members to move the pair of jaw members between a spaced apart configuration and an approximated configuration upon actuation of the trigger;
      a ratchet assembly disposed within the housing of the handle assembly, the ratchet assembly including:
         a first rack operatively coupled to the drive bar, the first rack defining a plurality of first rack teeth and having a distal end and a proximal end, wherein the first rack includes a first length between the distal end and the proximal end thereof;
         a second rack operatively coupled to the drive bar, spaced apart from the first rack, the second rack defining a plurality of second rack teeth and having a distal end and a proximal end, wherein the second rack includes a second length between the distal end and the proximal end thereof, the second length of the second rack being less than the first length of the first rack;
         a first pawl mounted within the housing of the handle assembly, the first pawl being selectively engagable with the plurality of first rack teeth of the first rack in a first position thereof;
         a second pawl mounted within the housing of the handle assembly, the second pawl being selectively engageable with the plurality of second rack teeth of the second rack in a first position thereof; and
         a distal well disposed adjacent the distal end of the first rack, wherein the first pawl is located in the distal well in an un-actuated position of the trigger.

2. The endoscopic surgical clip applier according to claim 1, wherein the ratchet assembly further includes a proximal well disposed between the proximal end of the first rack and the distal end of the second rack, wherein the second pawl is located in the proximal well in the un-actuated position of the trigger.

3. The endoscopic surgical clip applier according to claim 2, wherein the first rack is disposed in a position distal of the second rack.

4. The endoscopic surgical clip applier according to claim 1, wherein the ratchet assembly further includes a release switch at least partially supported within the housing of the handle assembly and operatively associated with the first pawl, the release switch selectively actuatable to move the first pawl from the first position, wherein the first pawl is in registration with the plurality of first rack teeth of the first rack to a second position, wherein the first pawl is out of registration with the plurality of first rack teeth of the first rack.

5. The endoscopic surgical clip applier according to claim 4, wherein the ratchet assembly further includes a release spring supported in the handle assembly, the release spring operatively associated with the release switch and biased to return the release switch to a home position such that the release switch is disengaged from the first pawl.

6. The endoscopic surgical clip applier according to claim 5, wherein when the release switch is actuated, the second pawl maintains registration with the plurality of second rack teeth of the second rack, in the first position thereof, until the second pawl is disposed in the proximal well or until the second pawl is disposed proximally beyond the proximal end of the second rack.

7. The endoscopic surgical clip applier according to claim 6, wherein the drive bar is longitudinally movable upon actuation of the trigger, wherein as the drive bar is moved longitudinally in a first direction, and the release switch is not actuated, the first pawl and the second pawl are moved over the plurality of first rack teeth and the plurality of second rack teeth of the first and the second racks, respectively, such that longitudinal movement of the drive bar in a second, opposite, direction is prevented until the first pawl is disposed in the distal well and the second pawl is disposed in the proximal well or until the first pawl is disposed at the proximal end of the first rack and the second pawl is disposed proximally beyond the proximal end of the second rack.

8. The endoscopic surgical clip applier according to claim 6, wherein the drive bar is longitudinally movable upon actuation of the trigger, wherein as the drive bar is moved longitudinally in a first direction, and the release switch is actuated to move the first pawl out of registration with the plurality of first rack teeth of the first rack, longitudinal movement of the drive bar in a second, opposite, direction is prevented until the second pawl is disposed in the proximal well or until the second pawl is disposed proximally beyond the proximal end of the second rack.

9. The endoscopic surgical clip applier according to claim 8, wherein as the drive bar is moved longitudinally in the first direction, and the release switch is actuated to move the first pawl out of registration with the plurality of first rack teeth of the first rack, the second pawl is disposed beyond the proximal end of the second rack as the trigger reaches a partially actuated position, wherein the drive bar is longitudinally movable in the second, opposite, direction, as the trigger reaches a fully un-actuated position from the partially actuated position.

10. The endoscopic surgical clip applier according to claim 9, wherein the endoscopic assembly further comprises a plurality of surgical clips slidably disposed within the shaft assembly and selectively formable between the pair of jaw members, wherein when the first pawl is in the first position, the first pawl is in registration with the first rack disposed on the drive bar such that upon actuation of the trigger, the trigger is prevented from reversing the direction of movement thereof until the trigger is moved to a fully actuated position and a distal most surgical clip of the plurality of surgical clips is fully formed between the pair of jaw members.

11. The endoscopic surgical clip applier according to claim 10, wherein when the first pawl housing is in the second position, the first pawl is out of registration with the first rack disposed on the drive bar such that when the second pawl is disposed beyond the proximal end of the second rack and the trigger is moved to the partially actuated position, the trigger is capable of reversing the direction of movement thereof such that the distal most surgical clip of the plurality of surgical clips is partially formed between the pair of jaw members.

12. The endoscopic surgical clip applier according to claim 9, wherein the first pawl includes a lockout member extending therefrom, the lockout member provided to selectively engage the release switch, as the trigger moves to the fully un-actuated position, to prevent the release switch from moving the first pawl out of registration with the plurality of first rack teeth of the first rack, to the second position thereof.

13. The endoscopic surgical clip applier according to claim 1, wherein the ratchet assembly further includes a first pawl spring and a second pawl spring supported within the housing of the handle assembly, the first pawl spring being configured to bias the first pawl into engagement with the plurality of first rack teeth of the first rack and the second pawl spring being configured to bias the second pawl into engagement with the plurality of second rack teeth of the second rack.

14. An endoscopic surgical clip applier, comprising:
an endoscopic assembly including:
a shaft assembly; and
a pair of jaw members operatively coupled to, and extending from the shaft assembly; and
a handle assembly including:
a housing selectively connectable to the endoscopic assembly;
a fixed handle extending from the housing;
a trigger pivotally connected to the fixed handle;
a drive bar disposed within the housing of the handle assembly and operatively coupled to the trigger and the pair of jaw members to move the pair of jaw members between a spaced apart configuration and an approximated configuration upon actuation of the trigger; and
a ratchet assembly disposed within the housing of the handle assembly, the ratchet assembly including:
a first rack defined on a top portion of the drive bar, the first rack including a plurality of first rack teeth and having a distal end and a proximal end;
a second rack defined on the top portion of the drive bar, the second rack including a plurality of second rack teeth and having a distal end and a proximal end;
a first pawl movably mounted within the handle assembly and being selectively engageable with the plurality of first rack teeth of the first rack; and
a second pawl movably mounted within the handle assembly and being selectively engageable with the plurality of second rack teeth of the second rack, wherein upon movement of the trigger, a reversal of a direction of movement of the trigger is prohibited until the second pawl is disposed distally beyond the distal end of the second rack or proximally beyond the proximal end of the second rack.

15. The endoscopic surgical clip applier according to claim 14, wherein the first rack includes a first length between the distal end and the proximal end thereof, and wherein the second rack includes a second length between the distal end and the proximal end thereof, the second length of the second rack being less than the first length of the first rack.

16. The endoscopic surgical clip applier according to claim 14, wherein the ratchet assembly further includes a release switch at least partially supported within the housing of the handle assembly and operatively associated with the first pawl, the release switch selectively actuatable to move the first pawl from a first position, wherein the first pawl is in registration with the plurality of first rack teeth of the first rack, to a second position, wherein the first pawl is out of registration with the plurality of first rack teeth of the first rack.

17. The endoscopic surgical clip applier according to claim 16, wherein when the release switch is disengaged from the first pawl such that the first pawl remains in the first position, upon movement of the trigger, the reversal of the direction of movement of the trigger is prohibited until the first pawl is disposed distally beyond the distal end of the first rack or disposed at the proximal end of the first rack.

* * * * *